United States Patent
Krapp et al.

(10) Patent No.: US 10,531,658 B2
(45) Date of Patent: Jan. 14, 2020

(54) NONAQUEOUS PESTICIDE SUSPENSION COMPRISING A WATER SOLUBLE SOLVENT, AN INORGANIC THICKENER, AND AN ALKOXYLATE

(71) Applicant: BASF SE, Ludwigshafen am Rhein (DE)

(72) Inventors: Michael Krapp, Altrip (DE); Wen Xu, Cary, NC (US); Galen Tsun, Foster City, CA (US); Marine Minvielle, Durham, NC (US)

(73) Assignee: BASF SE, Ludwigshafen am Rhein ( * ) Notice: Subject to any disclaimer, the term of this patent is extended or adjusted under 35 U.S.C. 154(b) by 18 days.

(21) Appl. No.: 15/749,857

(22) PCT Filed: Aug. 11, 2016

(86) PCT No.: PCT/EP2016/069095
§ 371 (c)(1),
(2) Date: Feb. 2, 2018

(87) PCT Pub. No.: WO2017/025581
PCT Pub. Date: Feb. 16, 2017

(65) Prior Publication Data
US 2018/0220644 A1 Aug. 9, 2018

Related U.S. Application Data

(60) Provisional application No. 62/204,818, filed on Aug. 13, 2015.

(30) Foreign Application Priority Data

Jul. 7, 2016 (EP) ..................... 16178322

(51) Int. Cl.
| | | |
|---|---|---|
| A01N 25/04 | (2006.01) |
| A01N 57/20 | (2006.01) |
| A01N 37/22 | (2006.01) |
| A01N 43/90 | (2006.01) |
| A01N 47/28 | (2006.01) |
| A01N 47/40 | (2006.01) |

(52) U.S. Cl.
CPC ............ *A01N 25/04* (2013.01); *A01N 37/22* (2013.01); *A01N 43/90* (2013.01); *A01N 47/28* (2013.01); *A01N 47/40* (2013.01); *A01N 57/20* (2013.01)

(58) Field of Classification Search
None
See application file for complete search history.

(56) References Cited

U.S. PATENT DOCUMENTS

| | | |
|---|---|---|
| 5,906,962 A | 5/1999 | Pallas et al. |
| 2002/0065198 A1 | 5/2002 | Highsmith et al. |
| 2017/0105409 A1 | 4/2017 | Auweter et al. |

FOREIGN PATENT DOCUMENTS

| | | |
|---|---|---|
| CN | 101692807 A | 4/2010 |
| EP | 0420497 A1 | 4/1991 |
| WO | 2010034737 | 4/2010 |
| WO | 2012084670 A1 | 6/2012 |
| WO | 2012143317 A1 | 10/2012 |
| WO | 2015055497 A1 | 4/2015 |
| WO | 2015103190 A1 | 7/2015 |
| WO | 2015103195 A1 | 7/2015 |
| WO | 2015172938 A1 | 11/2015 |
| WO | 2015173029 A1 | 11/2015 |
| WO | 2016008696 A1 | 1/2016 |
| WO | 2016016042 A1 | 2/2016 |
| WO | 2016091801 A1 | 6/2016 |
| WO | 2017025582 A1 | 2/2017 |

OTHER PUBLICATIONS

International Search Report and Written Opinion for International Application No. PCT/EP2016/069095, dated Oct. 7, 2016, 10 pages.
Raghavan et al. "Rheology of Silica Dispersions in Organic Liquids: New Evidence for Solvation Forces Dictated by Hydrogen Bonding", Langmuir, 2000, pp. 7920-7930, vol. 16 (No. 21).

*Primary Examiner* — Alton N Pryor
(74) *Attorney, Agent, or Firm* — Armstrong Teasdale LLP

(57) ABSTRACT

A liquid nonaqueous composition is disclosed. The composition includes: a pesticide in form of suspended particles, a water soluble solvent, an inorganic thickener, and an alkoxylate. A method for the preparation of the composition is also disclosed. The method includes contacting the pesticide with the water soluble solvent, the inorganic thickener, and the alkoxylate. The method may further include contact with a block polymer surfactant and/or a nonionic cosurfactant. A method for controlling phytopathogenic fungi and/or undesired plant growth and/or undesired attack by insects or mites and/or for regulating the growth of plants, wherein the composition is allowed to act on a particular pest, their habitat or plants to be protected from the particular pest, on soil and/or on undesired plants and/or useful plants and/or their habitat.

19 Claims, No Drawings

NONAQUEOUS PESTICIDE SUSPENSION COMPRISING A WATER SOLUBLE SOLVENT, AN INORGANIC THICKENER, AND AN ALKOXYLATE

CROSS-REFERENCE TO RELATED APPLICATIONS

This application is a U.S. National Phase Application of PCT/EP2016/069095, filed Aug. 11, 2016, which claims the benefit of priority to EP Application No. 16178322.0, filed Jul. 7, 2016, and U.S. Provisional Application No. 62/204,818, filed Aug. 13, 2015, the contents of which are hereby expressly incorporated by reference in their entirety.

The present invention relates to a liquid nonaqueous composition comprising a pesticide in the form of suspended particles, a water soluble solvent, a inorganic thickener, and an alkoxylate. The present invention further relates to a liquid nonaqueous composition comprising a pesticide in the form of suspended particles, a propylene glycol solvent, an inorganic thickener, and an alkoxylated alkanol. The present invention relates to a liquid nonaqueous composition comprising a pesticide in the form of suspended particles, a water soluble solvent, a inorganic thickener, and a alkoxylate, which is preferably water-insoluble. The present invention relates to a liquid nonaqueous composition comprising a pesticide in the form of suspended particles, where the water soluble solvent may be a propylene glycol solvent and where the inorganic thickener may comprise silica particles. It further relates to a method for the preparation of said composition, where the pesticide, the water soluble solvent, the inorganic thickener, the alkoxylated alkanol, optionally the block polymer surfactant, and optionally the cosurfactant are contacted. It further relates to a method for controlling phytopathogenic fungi and/or undesired plant growth and/or undesired attack by insects or mites and/or for regulating the growth of plants, where said composition is allowed to act on the particular pests, their habitat or the plants to be protected from the particular pest, the soil and/or on undesired plants and/or the useful plants and/or their habitat; and finally to seed treated with said composition. The present invention comprises combinations of preferred features with other preferred features.

Agrochemical formulations in form of aqueous suspensions are known and may contain large amounts of water as continuous phase for suspending pesticide particles. However, such aqueous formulations have various drawbacks, e.g. they are not suitable for pesticides which degrade in aqueous phase slowly; pesticides having an increased water solubility may not be suspended; formulation additives need to be water-soluble; or microbial growth is high in aqueous systems. Object of the present invention was to overcome these and other drawbacks.

One embodiment of the present invention is a liquid nonaqueous composition comprising a pesticide in form of suspended particles, a water soluble solvent, an inorganic thickener, and a alkoxylate, which is preferably water-insoluble. The water soluble solvent may comprise one or more of the following: propylene glycol, ethylene glycol, polyethylene glycol, polypropylene glycol, glycerin, propylene carbonate, ethylene carbonate, butylene carbonate, and dimethyl sulfoxide. The alkoxylate may comprise one or more compound(s) may comprise (a) ethoxylated and propoxylated C12-18 alcohols; (b) polyglycols based on ethylene oxide(s) and/or propylene oxide(s); and (c) polyalkyleneoxide modified heptamethyltrisiloxane. The inorganic thickener may be silica. In another embodiment the composition may further comprise a block polymer surfactant. The block polymer surfactant may be an alkoxylate block polymer, which comprises blocks of polyethylene oxide and polypropylene oxide. A further embodiment of the current application is a method for the preparation of the composition described in the present invention, where the pesticide, the water soluble solvent, the inorganic thickener, the water insoluble alkoxylate, optionally the block polymer surfactant, and optionally the cosurfactant are contacted. A further embodiment of the current invention is a method for controlling phytopathogenic fungi and/or undesired plant growth and/or undesired attack by insects or mites and/or for regulating the growth of plants, where the composition described herein is allowed to act on the particular pests, their habitat or the plants to be protected from the particular pest, the soil and/or on undesired plants and/or the useful plants and/or their habitat. A further embodiment of the current invention is a seed treated with the composition as described herein.

The object of the current invention was achieved by a liquid nonaqueous composition comprising a pesticide in form of suspended particles, a water soluble solvent, an inorganic thickener, and an alkoxylate, preferably an alkoxylated alkanol.

The composition is a liquid composition, which may be liquid at 20° C. The composition usually comprises a continuous liquid phase and a suspended solid phase. The liquid phase usually comprises the water soluble solvent, such as propylene glycol. The solid phase usually forms solid particles within the liquid phase. The solid phase usually comprises the pesticide particles.

The composition is a nonaqueous composition. The composition usually comprises less than 5 wt %, preferably less than 1 wt %, and in particular less than 0.3 wt % of water. In another form the composition is essentially free of water.

The term "water soluble" or "hydophillic" means the compound may have a solubility in water at 20° C. of at least 5 g/l, preferably of at least 20 g/l, more preferably at least 50 g/l, and in particular of at least 100 g/l.

The term "water insoluble" or "hydrophobic" means the compound may have a solubility in water at 20° C. of up to 100 g/l, preferably of up to 50 g/l ° C., more preferably up to 20 g/l, and in particular of up to 5 g/l.

The term pesticide refers usually to at least one active substance selected from the group of the fungicides, insecticides, nematicides, herbicides, safeners, biopesticides and/or growth regulators. Preferred pesticides are fungicides, insecticides, herbicides and growth regulators. Especially preferred pesticides are insecticides. Mixtures of pesticides of two or more of the abovementioned classes may also be used. The skilled worker is familiar with such pesticides, which can be found, for example, in the Pesticide Manual, 16th Ed. (2013), The British Crop Protection Council, London. Suitable insecticides are insecticides from the class of the carbamates, organophosphates, organochlorine insecticides, phenylpyrazoles, pyrethroids, neonicotinoids, spinosins, avermectins, milbemycins, juvenile hormone analogs, alkyl halides, organotin compounds nereistoxin analogs, benzoylureas, diacylhydrazines, METI acarizides, and insecticides such as chloropicrin, pymetrozin, flonicamid, clofentezin, hexythiazox, etoxazole, diafenthiuron, propargite, tetradifon, chlorofenapyr, DNOC, buprofezine, cyromazine, amitraz, hydramethylnon, acequinocyl, fluacrypyrim, rotenone, or their derivatives. Suitable fungicides are fungicides from the classes of dinitroanilines, allylamines, anilinopyrimidines, antibiotics, aromatic hydrocarbons, benzenesulfonamides, benzimidazoles, benzisothiazoles, benzophenones, benzothiadiazoles, benzotriazines, benzyl carbamates, carbamates, carboxamides, carboxylic acid diamides, chloronitriles cyanoacetamide oximes, cyanoimidazoles, cyclopropanecarboxamides, dicarboximides, dihydrodioxazines, dinitrophenyl crotonates, dithiocarbamates, dithiolanes, ethylphosphonates, ethylaminothiazolecarboxamides, guanidines, hydroxy-(2-amino)pyrimidines, hydroxyanilides, imidazoles, imidazolinones, inorganic substances, isobenzofuranones, methoxyacrylates, methoxycarbamates, morpholines, N phenylcarbamates, oxazolidinediones, oximinoacetates, oximinoacetamides, peptidylpyrimidine nucleosides, phenylacetamides, phenylamides, phenylpyrroles, phenylureas, phosphonates, phosphorothiolates, phthalamic acids, phthalimides, piperazines, piperidines, propionamides, pyridazinones, pyridines, pyridinylmethylbenzamides, pyrimidinamines, pyrimidines, pyrimidinonehydrazones, pyrroloquinolinones, quinazolinones, quinolines, quinones, sulfamides, sulfamoyltriazoles, thiazolecarboxamides, thiocarbamates, thiophanates, thiophenecarboxamides, toluamides, triphenyltin compounds, triazines, triazoles. Suitable herbicides are herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ether, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, ureas. Mixtures of different pesticides are also suitable.

In one form the pesticide is metaflumizone. In another form the pesticide is abamectin. In another form the pesticide is glyphosate acid. In another form the pesticide is dinotefuran. In another form the pesticide is broflanilide. In another form the pesticide is an active compound of the formula I

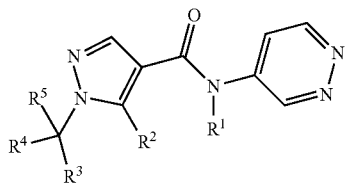

I wherein
$R^1$ is H, $C_1$-$C_2$-alkyl, or $C_1$-$C_2$-alkoxy-$C_1$-$C_2$-alkyl;
$R^2$ is $CH_3$, or halomethyl;
$R^3$ is CN, $C_1$-$C_6$-alkyl, $C_1$-$C_6$-haloalkyl, $C_1$-$C_2$-alkoxy-$C_1$-$C_2$-alkyl, $C_2$-$C_6$-alkenyl and $C_2$-$C_6$-alkynyl, $C_3$-$C_6$-cycloalkyl, $C_5$-$C_6$-cycloalkenyl, $C_1$-$C_6$-alkoxy, wherein the C-atoms are unsubstituted, or partially or fully substituted by $R^a$;
$R^a$ is halogen, CN, $C_1$-$C_2$-alkyl, $C_1$-$C_2$-haloalkyl, $C_1$-$C_4$-alkoxy, $C_1$-$C_2$-haloalkoxy;

$R^4$ is $C_1$-$C_4$-alkyl, or a group mentioned for $R^3$; or
$R^3$ and $R^4$ may together form $C_5$-$C_6$-cycloalkyl, which is unsubstituted, or partially or fully substituted by $R^a$;
$R^5$ is H, or a group mentioned for $R^4$.

Suitable examples for the active compound of the formula I are 1-isopropyl-N,5-dimethyl-N-pyridazin-4-yl-pyrazole-4-carboxamide; 1-(1,2-dimethylpropyl)-N-ethyl-5-methyl-N-pyridazin-4-yl-pyrazole-4-carboxamide; N,5-dimethyl-N-pyridazin-4-yl-1-(2,2,2-trifluoro-1-methyl-ethyl) pyrazole-4-carboxamide; 1-[1-(1-cyanocyclopropyl)ethyl]-N-ethyl-5-methyl-N-pyridazin-4-yl-pyrazole-4-carboxamide; N-ethyl-1-(2-fluoro-1-methyl-propyl)-5-methyl-N-pyridazin-4-yl-pyrazole-4-carboxamide; 1-(1,2-dimethylpropyl)-N,5-dimethyl-N-pyridazin-4-yl-pyrazole-4-carboxamide; 1-[1-(1-cyanocyclopropyl)ethyl]-N,5-dimethyl-N-pyridazin-4-yl-pyrazole-4-carboxamide; N-methyl-1-(2-fluoro-1-methyl-propyl)-5-methyl-N-pyridazin-4-yl-pyrazole-4-carboxamide; 1-(4,4-difluorocyclohexyl)-N-ethyl-5-methyl-N-pyridazin-4-yl-pyrazole-4-carboxamide; or 1-(4,4-difluorocyclohexyl)-N,5-dimethyl-N-pyridazin-4-yl-pyrazole-4-carboxamide. These compounds are known from WO2010/034737, WO2012/084670, WO2012/143317, and WO2015/055497, respectively.

The pesticide may have a melting point of at least 40° C., at least 50° C., preferably of at least 70° C. and in particular of at least 90° C.

The pesticide may have a solubility in water at 20° C. of at least 0.5 g/l, preferably of at least 2 g/l ° C., more preferably at least 10 g/l and in particular of at least 50 g/l. The pesticide may have a solubility in water at 20° C. of up to 250 g/l, up to 250 g/l, up to 150 g/l or up to 80 g/l. In a preferred form the pesticide may have a solubility in water at 20° C. of up to 10 g/l, up to 5 g/l, up to 1 g/l ° C. or up to 0.5 g/l.

The pesticide may be present in the form of crystalline or amorphous particles which are solid at 20° C. The pesticide has a usually particle size distribution with an Dx50 value of from 0.01 to 50 µm, from 0.1 to 10 µm, preferably 0.2 µm to 5 µm and especially preferably 0.5 µm to 2 µm. The particle size distribution can be determined by laser light diffraction of an aqueous suspension comprising the particles. The sample preparation, for example the dilution to the measuring concentration, will, in this measuring method, depend on the fineness and concentration of the active substances in the suspension sample and on the apparatus used (for example Malvern Mastersizer), inter alia. The procedure should be developed for the system in question and is known to a person skilled in the art.

The composition may comprise at least one further pesticide in addition to the pesticide. The further pesticide may be present in form of suspended particles and/or in dissolved form. Preferably, the further pesticide may be present in form of suspended particles. In another preferred form the further pesticide may be present in dissolved form. The further pesticide may be selected from the aforementioned list of pesticides.

The composition may comprise from 1 to 50 wt %, preferably from 5 to 35 wt %, and in particular from 10 to 30 wt % total sum of the pesticide and the further pesticide. In another form the composition may comprise at least 0.1 wt %, preferably at least 1 wt %, and in particular at least 10 wt % total sum of the pesticide and the further pesticide.

The water soluble solvent may include one or more of the following: propylene glycol, ethylene glycol, polyethylene glycol, polypropylene glycol, glycerin, propylene carbonate, ethylene carbonate, butylene carbonate, and dimethyl sulfoxide. In another form the water soluble solvent may comprise propylene glycol, ethylene glycol, polyethylene glycol, or glycerin. In another form the water soluble solvent may comprise propylene glycol, polyethylene glycol, or glycerin. Mixtures of different water soluble solvents are also suitable. The water soluble solvent comprises preferably propylene glycol (1,2-propylene glycol) or polyethylene glycol. The water soluble solvent comprises in particular propylene glycol (e.g. 1,2-propylene glycol).

The water soluble solvent may have a solubility in water at 20° C. of at least 10 g/l, preferably of at least 50 g/l ° C., more preferably at least 100 g/l and in particular of at least 200 g/l.

The propylene glycol may be 1,2-propylene glycol or 1,3-propylene glycol. Preferably, the propylene glycol is 1,2-propylene glycol. The polyethylene glycol has usually a melting point of up to 25° C., preferably up to 20° C., and in particular up to 15° C. The polyethylene glycol has usually a average molar mass of up to 1000 g/mol, preferably up to 700 g/mol and in particular up to 500 g/mol.

The composition may comprise at least 5 wt %, preferably at least 10 wt %, and in particular at least 15 wt % of the water soluble solvent. The composition may comprise from 1 to 50 wt %, preferably from 5 to 40 wt %, and in particular from 10 to 30 wt % of the water soluble solvent. In another form the composition may comprise from 1 to 90 wt %, preferably from 5 to 85 wt %, and in particular from 15 to 80 wt % of the water soluble solvent. In another form the water soluble solvent is added in an amount to fill up the composition to 100 wt %.

The sum of the amounts of the water soluble solvent (e.g. propylene glycol) and the alkoxylate (e.g. the alkoxyalted alkanol) is usually at least 25 wt %, preferably at least 35 wt %, and in particular at least 40 wt % of the composition.

The composition may comprise further organic solvent in addition to the water soluble solvent. Suitable further organic solvents are mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. benzylalcohol, cyclohexanol; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof. The composition may comprise up to 10 wt %, preferably up to 3 wt %, and in particular up to 1 wt % of the further organic solvents. In one form the composition is essentially free of the further organic solvent. Typically, the further organic solvent is water-insoluble.

The inorganic thickener may be present in form of particles, which may be water dispersible. Preferably, the inorganic thickener is present in form of suspended particles. Preferably, the inorganic thickener comprises clay particles (organically modified or unmodified), or silica particles, more preferably fumed silica particles, and in particular hydrophilic silica particles. In a preferred form the inorganic thickener comprises silica particles, in particular fumed silica particles.

In general silica is available as fumed silica and precipitated silica. Precipitated silica is typically produced by precipitation from a solution containing silicate salts, such as by the reaction of an alkaline silicate solution with a mineral acid. Fumed silica (also known as pyrogenic silica) is typically produced by flame pyrolysis of silicon tetrachloride or from quartz sand vaporized in an about 3000° C. hot electric arc. Fumed silica and precipitated silica clearly differ in their chemical, physical and structural properties, and are thus used for different industrial purposes. For example precipitated silica has a lot of pores with a pore size of up to 30 nm, whereas fumed silica is usually free of such pores. The inorganic thickener may be selected from fumed silica particles which are preferably free of pores (e.g. of pores with a pore size of up to 30 nm).

In general silica particles are available as hydrophilic silica particles or as hydrophobic modified silica particles. In general silica is hydrophilic due to silanol (Si—OH) groups on the surface of the particles. These silanol groups may be chemically reacted with various reagents to render the silica hydrophobic. The hydrophobic modified silica particles are usually modified by treatment with a silane, a siloxane, or a mixture thereof. Examples for silanes or siloxanes are dimethyldichlorosilane, octamethylcyclotetrasiloxane, polydimethylsiloxane, octylsilane, hexamethyldisiloxane, methacrylsilane.

In the present invention the inorganic thickener is selected from fumed silica particles which are preferably hydrophilic silica particles. Preferably, the silica particles are not hydrophobic silica particles. Preferably the silica particles are not modified by treatment with a silane, a siloxane, or a mixture thereof. Preferably the silica particles are free of a modification by treatment with a silane, a siloxane, or a mixture thereof. The composition may be essentially free of hydrophobic modified silica particles (e.g. hydrophobic modified silica particles modified by treatment with a silane, a siloxane, or a mixture thereof).

Typically, the inorganic thickener contains particles (e.g. silica particles) with specific surface area in the range from 50 to 500 m$^2$/g, preferably from 100 to 350 m$^2$/g, and in particular from 170 to 230 m$^2$/g. In another form the inorganic thickener contains silica particles with specific surface area in the range from 50 to 600 m$^2$/g, preferably from 140 to 450 m$^2$/g, and in particular from 170 to 350 m$^2$/g. In another form the inorganic thickener contains silica particles with specific surface area of at least 50 m$^2$/g, preferably at least 80 m$^2$/g, and in particular at least 120 m$^2$/g. The specific surface area may refer to the BET surface area. The specific surface area may be determined according to DIN ISO 9277.

In general, a distinction is made in the case of particles between the primary and the secondary particle diameter. A plurality of smaller particles (having a primary particle diameter) may agglomerate to form a larger particle (having a secondary particle diameter). The secondary particle diameter can therefore often also be designated as agglomerate size.

Typically, the inorganic thickener contains particles (e.g. silica particles) with a primary particle diameter in the range from 0.1 to 500 nm, preferably from 1 to 100 nm, in particular from 5 to 25 nm. The primary particle diameter is preferably determined via transmission electron microscopy (TEM).

Typically, the pH value of an aqueous dispersion of the silica particles is in the range from 1 to 5.5, preferably in the range from 2 to 5.0, and in particular in the range from 3 to 4.8. The pH value is usually determined as a 4 wt % dispersion of the silica particles in water.

The silica particles may comprise at least 95 wt %, preferably at least 98 wt %, and in particular at least 99.3 wt % of $SiO_2$.

The weight loss on ignition (also called the ignition loss) of the silica particles is up to 5 wt %, preferably up to 4.0 wt %, and in particular up to 2.1 wt %. The ignition loss may be determined at 1000° C. (e.g. 2 hours at 1000° C.).

The composition may comprise up to 5 wt %, preferably up to 2.5 wt %, and in particular up to 1.5 wt % of the inorganic thickener (e.g. silica particles). In another form the composition may comprise up to 1.5 wt %, preferably up to 1.0 wt %, and in particular up to 0.8 wt % of the inorganic thickener (e.g. silica particles). The composition may comprise from 0.01 to 5 wt %, preferably from 0.05 to 2.5 wt %, and in particular from 0.1 to 1.5 wt % of the inorganic thickener (e.g. silica particles). In another form the composition may comprise from 0.01 to 3.0 wt %, preferably from 0.05 to 1.0 wt %, and in particular from 0.1 to 0.8 wt % of the inorganic thickener (e.g. silica particles).

Suitable alkoxylates (e.g. water insoluble alkoxylates) include, but are not limited to: polyglycols based on ethylene oxide(s) and/or propylene oxide(s); fatty oleyl alcohols and polyalkyleneoxide modified peptamethyltrisiloxane. Preferably, the alkoxylate is an alkoxylated alkanol.

In another form suitable alkoxylates include alkoxylated alkanols, which are usually alkoxylated linear or branched, saturated or unsaturated $C_1$-$C_{20}$ (preferably $C_8$-$C_{20}$) alkanols, preferably ethoxylated, ethoxylated and propoxylated, or ethoxylated and butoxylated, linear or branched, saturated $C_2$-$C_{18}$ (preferably $C_8$-$C_{18}$) alkanols or more preferably, ethoxylated and propoxylated $C_4$-$C_{18}$ (preferably $C_{12}$-$C_{20}$) alkanols. The alkanol unit of the alkoxylated alkanol may be a technical mixture of various chain lengths and isomers. The total number of alkoxy units in the alkoxylated alkanols may range from 5 to 30, preferably from 10 to 25 alkoxy units (e.g. ethyleneoxy and/or propyleneoxy units). The alkoxy units (e.g. EO and PO units) occur preferably in block sequence, in particular as diblock sequence. The polyalkoxylate chain of the alkoxylated alkanols may be terminated by a hydroxy group or a $C_1$ to $C_4$ alkyl, wherein the hydroxy group is preferred. In another form the alkoxy units (e.g. EO and PO units) occur preferably in block sequence, in particular as diblock sequence, and the polyalkoxylate chain of the alkoxylated alkanols is terminated by a hydroxy group.

In another form preferred suitable alkoxylates are alkoxylated alkanols of the formula (I)

$$R^a\text{—O-}(AO)_m\text{—}R^1 \quad (I)$$

in which $R^a$ is straight-chain or branched alkyl or alkylene with from 1 to 32, preferably 4 to 32, more preferably from 10 to 22, carbon atoms, AO is an ethylene oxide radical, propylene oxide radical, butylene oxide radical, pentylene oxide radical, styrene oxide radical or mixtures of the abovementioned radicals in random or block sequence (wherein a diblock sequence is preferred), m is numbers from 1 to 30 and $R^1$ is hydrogen or alkyl with from 1 to 4 carbon atoms.

Particularly preferred alkoxylated alkanols are those of the formula (II)

$$R^b\text{—O-}(EO)_p\text{—}(PO)_q\text{—}R^1 \quad (II)$$

in which $R^b$ is straight-chain or branched alkyl or alkylene with from 1 to 32, preferably 4 to 32, more preferably from 10 to 22, particularly preferably from 6 to 18, carbon atoms, EO is —$CH_2CH_2$—O—, PO is —$CH_2$—$CH(CH_3)$—O— or —$(CH_2)_3$—O—, p is numbers from 1 to 20, preferably from 2 to 15, q is numbers from 1 to 25, preferably from 5 to 20, and $R^1$ is hydrogen or alkyl with from 1 to 4 carbon atoms, in which the EO and PO units can occur in random sequence or as blocks.

The alkoxylated alkanol may have a solidification temperature of below 50° C., preferably of below 20° C. and in particular of below 0° C.

The composition may comprise at least 5 wt %, at least 10 wt %, preferably at least 15 wt %, and in particular at least 20 wt % of the alkoxylate (e.g. the alkoxylated alkanol). In another form the composition may comprise at least 0.1 wt %, at least 0.5 wt %, preferably at least 1 wt %, and in particular at least 1.5 wt % of the alkoxylate (e.g. the alkoxylated alkanol). The composition may comprise from 1 to 50 wt %, preferably from 10 to 40 wt %, and in particular from 20 to 35 wt % of the alkoxylate (e.g. the alkoxylated alkanol).

In one form the alkoxylate is a short chain alkoxylated alkanol, which is an alkoxylated alkanol of the formula I, in which $R^a$ is straight-chain or branched alkyl with from 1 to 8, preferably from 2 to 6, and in particular 3 to 5 carbon atoms. In another form the alkoxylate is a short chain alkoxylated alkanol, which is an alkoxylated alkanol of the formula II, in which $R^b$ is straight-chain or branched alkyl with from 1 to 8, preferably from 2 to 6, and in particular 3 to 5 carbon atoms. The composition may comprise at least 0.1 wt %, at least 0.5 wt %, preferably at least 1 wt %, and in particular at least 1.5 wt % of the short chain alkoxylated alkanol. The composition may comprise from 0.1 to 20 wt %, preferably from 0.5 to 15 wt %, and in particular from 1 to 8 wt % of the short chain alkoxylated alkanol.

The composition may comprise a block polymer surfactant. The block polymer surfactant may be a diblock polymer or a triblock polymer, wherein the triblock polymer is preferred. The blocks of the block polymer surfactant may be of the A-B or A-B-A type, where the A-B-A type is preferred. Typically, the block polymers surfactant is a nonionic surfactant.

The block polymer surfactant is preferably an alkoxylate block polymer, which may comprise blocks of polyethylene oxide and polypropylene oxide. The alkoxylate block polymers comprise usually at least 20 wt %, preferably at least 30 wt % of polymerized ethylene oxide. In a preferred form the alkoxylate block polymers comprise at least 10 wt %, preferably at least 15 wt % of polymerized ethylene oxide. The alkoxylate block polymers is preferably a block polymers A-B-A type comprising blocks of polyethylene oxide (block "A") and polypropylene oxide (block "B"). The alkoxylate block polymers are usually terminated on both ends by hydroxyl groups.

The molecular weight of the block polymer surfactant (e.g. the alkoxylate block polymer) may be from 1000 to 30000 Da, preferably from 2000 to 15000 Da.

The block polymer surfactant (e.g. the alkoxylate block polymer) may have a solubility in water at 20° C. of at least 3 wt %, preferably at least 5 wt %, and in particular at least 8 wt %.

The block polymer surfactant (e.g. the alkoxylate block polymer) may have a HLB value in the range from 8 to 22, preferably from 10 to 20. In another form the block polymer surfactant (e.g. the alkoxylate block polymer) may have a HLB value in the range from 1 to 10, preferably from 1 to 8. The HLB may be calculated by known methods.

In a preferred form the block polymer surfactant is an alkoxylate block polymer of the A-B-A type comprising blocks of polyethylene oxide (block "A") and polypropylene oxide (block "B"), and wherein the alkoxylate block polymer is terminated on both ends by hydroxyl groups.

The composition may comprise at least 7 wt %, preferably at least 12 wt %, and in particular at least 18 wt % of the block polymer surfactant (e.g. the alkoxylate block polymer). In another form the composition may comprise at least 3 wt %, preferably at least 5 wt %, and in particular at least 10 wt % of the block polymer surfactant (e.g. the alkoxylate block polymer). The composition may comprise from 5 to 40 wt %, preferably from 10 to 35 wt %, and in particular from 15 to 30 wt % of the block polymer surfactant (e.g. the alkoxylate block polymer). In another form the composition may comprise from 1 to 40 wt %, preferably from 5 to 35 wt %, and in particular from 10 to 30 wt % of the block polymer surfactant (e.g. the alkoxylate block polymer).

The sum of the amounts of the water soluble solvent, the alkoxylate, and the block polymer surfactant is usually at least 40 wt %, preferably at least 50 wt %, and in particular at least 60 wt % of the composition.

The composition may comprise a nonionic cosurfactant. The may have a HLB value in the range from 6 to 16, preferably from 8 to 16, and in particular from 8 to 14. The HLB may be calculated by known methods. Suitable cosurfactants are phenol alkoxylates, N-substituted fatty acid amides, amine oxides, esters, sugar-based surfactants, and mixtures thereof. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. The cosurfactant is usually different from the block polymer surfactant.

A preferred nonionic cosurfactant is a phenol alkoxylate, preferably a polyarylphenol alkoxylate, more preferably a polyarylphenol ethoxylate, and in particular a tristyrylphenol ethoxylate. The phenol alkoxylate may comprise at least 1 to 70, preferably 3 to 40, and in particular 5 to 30 alkylene oxide units (preferably ethylene oxide units). The phenol alkoxylate has usually a HLB value in the range from 7 to 17, preferably from 9 to 17, and in particular from 11 to 15.

The composition may comprise at least 3 wt %, preferably at least 7 wt %, and in particular at least 12 wt % of the nonionic cosurfactant (e.g. phenol alkoxylate, preferably the polyarylphenol alkoxylate). The composition may comprise from 1 to 35 wt %, preferably from 5 to 25 wt %, and in particular from 10 to 20 wt % of the nonionic cosurfactant (e.g. phenol alkoxylate, preferably the polyarylphenol alkoxylate).

The composition may comprise further surfactants in addition to the nonionic cosurfactant and the block polymer surfactant. Examples of further surfactants are listed in McCutcheon's, Vol. 1: Emulsifiers & Detergents, McCutcheon's Directories, Glen Rock, USA, 2008 (International Ed. or North American Ed.). Further surfactants may be anionic surfactants and cationic surfactants, wherein anionic surfactants are preferred.

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable cationic surfactants are quaternary surfactants, for example quaternary ammonium compounds with one or two hydrophobic groups, or salts of long-chain primary amines.

The further surfactant is preferably an anionic surfactant selected from sulfonates or sulfates, wherein sulfonates are preferred. The further surfactant is preferably selected from alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates, or from sulfates of fatty acids and oils, of ethoxylated alkylphenols, of alcohols, of ethoxylated alcohols, or of fatty acid esters. The further surfactant is more preferably selected from alkylarylsulfonates, sulfonates of condensed naphthalenes, sulfonates of naphthalenes and alkylnaphthalenes, wherein sulfonates of condensed naphthalenes are preferred.

The composition may comprise from 0.1 to 15 wt %, preferably from 1 to 10 wt %, and in particular from 2 to 8 wt % of the further surfactants (e.g. the anionic surfactant, preferably selected from sulfonates or sulfates).

In one form the alkoxylate is a short chain alkoxylated alkanol, and the composition comprises less than 5 wt %, preferably less than 1 wt % and in particular less than 0.1 wt % of the block polymer surfactant (e.g. the alkoxylate block polymer). In another form the alkoxylate is a short chain alkoxylated alkanol, and the composition is essentially free of the block polymer surfactant (e.g. the alkoxylate block polymer).

In one form the alkoxylate is a short chain alkoxylated alkanol, and the composition comprises a further surfactant, preferably selected from anionic surfactants (e.g. sulfonates or sulfates). In another form the alkoxylate is a short chain alkoxylated alkanol of the formula I, in which $R^a$ is straight-chain or branched alkyl or alkylene with from 1 to 8, preferably from 2 to 6, and in particular 3 to 5 carbon atoms, and the composition comprises a further surfactant selected from alkylarylsulfonates, sulfonates of condensed naphthalenes, sulfonates of naphthalenes and alkylnaphthalenes, wherein sulfonates of condensed naphthalenes are preferred.

In another form the alkoxylate is a short chain alkoxylated alkanol, wherein the composition comprises 0.1 to 20 wt %, preferably from 0.5 to 15 wt %, and in particular from 1 to 8 wt % of the short chain alkoxylated alkanol, and the composition comprises a further surfactant, preferably selected from anionic surfactants (e.g. sulfonates or sulfates), and the composition comprises 0.1 to 15 wt %, preferably from 1 to 10 wt %, and in particular from 2 to 8 wt % of the further surfactant. In one form the alkoxylate is a short chain alkoxylated alkanol, and the composition comprises a further surfactant, preferably selected from anionic surfactants (e.g. sulfonates or sulfates), and the composition is essentially free of the block polymer surfactant (e.g. the alkoxylate block polymer).

The composition may comprise further auxiliaries. Examples for suitable auxiliaries are anti-foaming agents, colorants, tackifiers and binders. Suitable anti-foaming agents are silicones, long chain alcohols, and salts of fatty acids. Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g.

alizarin-, azo- and phthalocyanine colorants). Suitable tackifiers or binders are polyvinylpyrrolidons, polyvinylacetates, polyvinyl alcohols, polyacrylates, biological or synthetic waxes, and cellulose ethers.

The composition may be used for the purposes of treatment of plant propagation materials, particularly seeds. The compositions in question give, after two-to-tenfold dilution, active substance concentrations of from 0.01 to 60% by weight, preferably from 0.1 to 40% by weight, in the ready-to-use preparations. Application can be carried out before or during sowing. Methods for applying or treating the compositions thereof, respectively, on to plant propagation material, especially seeds include dressing, coating, pelleting, dusting, soaking and in-furrow application methods of the propagation material. Preferably, the composition is applied on to the plant propagation material by a method such that germination is not induced, e. g. by seed dressing, pelleting, coating and dusting. When employed in plant protection, the amounts of the pesticide applied are, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha. In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seed) are generally required.

The user applies the composition according to the invention usually from a predosage device, a knapsack sprayer, a spray tank, a spray plane, or an irrigation system. Usually, the composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

The present invention further relates to a method of controlling phytopathogenic fungi and/or undesired plant growth and/or undesired insect or mite attack and/or for regulating the growth of plants, wherein the composition is allowed to act on the respective pests, their environment or the crop plants to be protected from the respective pest, on the soil and/or on undesired plants and/or on the crop plants and/or on their environment.

Examples of suitable crop plants are cereals, for example wheat, rye, barley, triticale, oats or rice; beet, for example sugar or fodder beet; pome fruit, stone fruit and soft fruit, for example apples, pears, plums, peaches, almonds, cherries, strawberries, raspberries, currants or gooseberries; legumes, for example beans, lentils, peas, lucerne or soybeans; oil crops, for example oilseed rape, mustard, olives, sunflowers, coconut, cacao, castor beans, oil palm, peanuts or soybeans; cucurbits, for example pumpkins/squash, cucumbers or melons; fiber crops, for example cotton, flax, hemp or jute; citrus fruit, for example oranges, lemons, grapefruit or tangerines; vegetable plants, for example spinach, lettuce, asparagus, cabbages, carrots, onions, tomatoes, potatoes, pumpkin/squash or capsicums; plants of the laurel family, for example avocados, cinnamon or camphor; energy crops and industrial feedstock crops, for example maize, soybeans, wheat, oilseed rape, sugar cane or oil palm; maize; tobacco; nuts; coffee; tea; bananas; wine (dessert grapes and grapes for vinification); hops; grass, for example turf; sweetleaf (Stevia rebaudania); rubber plants and forest plants, for example flowers, shrubs, deciduous trees and coniferous trees, and propagation material, for example seeds, and harvested produce of these plants.

The term crop plants also includes those plants which have been modified by breeding, mutagenesis or recombinant methods, including the biotechnological agricultural products which are on the market or in the process of being developed. Genetically modified plants are plants whose genetic material has been modified in a manner which does not occur under natural conditions by hybridizing, mutations or natural recombination (i.e. recombination of the genetic material). Here, one or more genes will, as a rule, be integrated into the genetic material of the plant in order to improve the plant's properties. Such recombinant modifications also comprise posttranslational modifications of proteins, oligo- or polypeptides, for example by means of glycosylation or binding polymers such as, for example, prenylated, acetylated or farnesylated residues or PEG residues.

The present invention further relates to seed containing the composition.

The present invention offers various advantages: Due to the low water content the composition is suitable for formulating pesticides which are sensitive to water; pesticides having an increased water solubility may be suspended; microbial growth is reduced; the storage stability is high; the freeze-thaw stability is high; easier to incorporate adjuvants (e.g. alkoxylates) into formulation; and efficacy of the composition is improved.

The examples which follow illustrate the invention without imposing any limitation.

EXAMPLES

Chemical stabilizer: liquid alkaline organic amine compound.
Sulfonate A: Sodium alkylnaphthalenesulfonate formaldehyde polycondensate, water soluble powder.
Thickener: White powder, hydrophilic, untreated, fumed silica, specific surface area (BET) about 200 m$^2$/g; average primary particle diameter 12 nm, tapped density about 0.05 kg/m$^3$, pH in water (4 wt %) about 3.8 to 4.6; ignition loss (1000° C.) up to 1.0 wt %; loss on drying up to 1.5 wt %; SiO$_2$ content at least 99.8 wt %.
Alkoxylate A: Short chain alkoxylated alkanol, nonionic ethoxylated and propoxylated (diblock sequence) butanol with HLB of 17, cloude point about 75° C., melting point about 30 to 35° C.
Alkoxylate B: liquid nonionic ethoxylated and propoxylated (diblock sequence) C12-18 aliphatic alcohol, water-insoluble, soluble in alcohols, solidification temperature about −5 to −8° C.
Cosurfactant A: nonionic ethoxylated tristyrylphenol surfactant, HLB 10-11.
Block Polymer A: nonionic EO-PO-EO Triblockcopolymer, average molecular weight about 6000 Da, ethylene oxide (EO) content about 40 wt %, melting point about 30-33° C., HLB 12-18, solubility in water at least 10 wt % at 25° C.
Insecticide A: 1-(1,2-dimethylpropyl)-N-ethyl-5-methyl-N-pyridazin-4-yl-pyrazole-4-carboxamide
Insecticide B: 1-[1-(1-cyanocyclopropyl)ethyl]-N-ethyl-5-methyl-N-pyridazin-4-yl-pyrazole-4-carboxamide
Insecticide C: N-ethyl-1-[(1S,2S)-2-fluoro-1-methyl-propyl]-5-methyl-N-pyridazin-4-yl-pyrazole-4-carboxamide

Example 1: Metaflumizone Suspension in Polyethylene Glycol Continuous Phase

A liquid metaflumizone suspension having the following composition was prepared:

| Component | Amount (wt/wt %) |
| --- | --- |
| Metaflumizone | 15 |
| Sulfonate A | 4 |
| Alkoxylate A | 2 |
| Thickener | 1.0 |
| Polyethylene Glycol | 78 |

The pesticidal suspension was prepared by following procedure:

1. Add metaflumizone, Sulfonate A, into Polyethylene Glycol (average molecular weight of 400) while agitating. Continue agitation until homogenous.
2. The above mixture was then wet milled using a bead mill to particle size around 2 μm.
3. Add Thickener to the above mixture, mixed until uniform.

Three prepared samples were stored under the following conditions: (a) one sample was stored at −10° C., (b) another sample was stored at F/T (daily cycling temperature from −10° C. to 30° C.) and (c) a third sample was stored at 54° C. for two weeks. The particle size was measured before/after storage by Malvern Mastersizer 2000.

The suspension stability was determined by visual observation of sample phase separation after storage as well as particle size increase before/after storage at different storage temperatures. It was found there is no increase in particle size at all above storage temperatures and no phase separation occurred, therefore, the suspension of metaflumizone was physically stable.

Example 2: Abamectin Suspension in Propylene Glycol Continuous Phase

An abamectin suspension having the following composition was prepared:

| Component | Amount (wt/wt %) |
| --- | --- |
| Abamectin | 20 |
| Cosurfactant A | 14 |
| Block Polymer A | 20 |
| Alkoxylate B | 10 |
| Thickener | 1.0 |
| 1,2-propylene glycol | 35 |

The pesticidal suspension was prepared by following procedure:

1. Add abamectin, Cosurfactant A, Block Polymer A, Alkoxylate B into the propylene glycol while agitating. Continue agitation until homogenous.
2. The above mixture was then wet milled using a bead mill to particle size around 2 μm.
3. Add Thickener to the above mixture, mix until uniform.

Three samples were stored and analyzed as described in Example 1. It was found there is no increase in particle size at all above storage temperatures and no significant phase separation occurred, therefore, the abamectin suspension was physically stable.

Example 3: Glyphosate Acid Suspension

A mixture of Dicamba Na salt and Glyphosate acid having the following composition was prepared:

| Component | Amount (wt/wt %) |
| --- | --- |
| Dicamba Na | 10 |
| Glyphosate acid | 20 |
| Sulfonate A | 4 |
| Alkoxylate A | 2 |
| Thickener | 1.0 |
| 1,2-propylene glycol | 63 |

The pesticidal suspension was prepared by following procedure:

1. Add Dicamba Na, Sulfonate A, Stabilizer into 1,2-propylene glycol while agitating. Continue agitation until Dicamba Na completely dissolved.
2. Add Glyphosate acid into above mixture while agitating. Continue agitation until homogenous.
3. The above mixture was then wet milled using a bead mill to particle size around 2 μm.
4. Add Thickener to the above mixture, mix until uniform.

Three samples were stored and analyzed as described in Example 1. It was found there is no increase in particle size at all above storage temperatures and no phase separation occurred, therefore, the suspension was physically stable.

Example 4: Metaflumizone Suspension in Propylene Glycol

Afidopyropen and formulation additives (except Thickener) were added into 1,2-propylene glycol while agitating. The agitation was continued until afidopyropen was completely dissolved. Then metaflumizone and Thickener was added into the mixture while agitating. The agitation was continued until homogenous. The mixture was then wet milled using a bead mill to particle size around 2 μm.

|  | Amount (wt/wt %) |
| --- | --- |
| Afidopyropen | 1.5 |
| Metaflumizone | 15 |
| Cosurfactant A | 14 |
| Block Polymer A | 16.3 |
| Alkoxylate B | 30 |
| Chemical stabilizer | 0.2 |
| Thickener | 1.0 |
| 1,2-propylene glycol | 22 |

Samples were stored and analyzed as in Example 1. It was found there was no increase in particle size at all storage temperatures and no phase separation occurred, therefore, the suspension was physically stable.

Example 5: Dinotefuran Suspension in Propylene Glycol

Afidopyropen and formulation additives (except Thickener) were added into 1,2-propylene glycol while agitating. The agitation was continued until afidopyropen was completely dissolved. Then dinotefuran and Thickener was added into the mixture while agitating. The agitation was continued until homogenous. The mixture was then wet milled using a bead mill to particle size around 2 μm.

|  | Amount (wt/wt %) |
| --- | --- |
| Afidopyropen | 1.4 |
| Dinotefuran | 13.6 |

-continued

| | Amount (wt/wt %) |
|---|---|
| Cosurfactant A | 14 |
| Block Polymer A | 22.3 |
| Alkoxylate B | 29 |
| Chemical stabilizer | 0.2 |
| Thickener | 1.5 |
| 1,2-propylene glycol | 18 |

Samples were stored and analyzed as in Example 1. It was found there was no increase in particle size at all storage temperatures and no phase separation occurred, therefore, the suspension was physically stable.

Example 6: Dinotefuran Suspension in Propylene Glycol

Afidopyropen and formulation additives (except Thickener) were added into 1,2-propylene glycol while agitating. The agitation was continued until afidopyropen was completely dissolved. Then dinotefuran and Thickener was added into the mixture while agitating. The agitation was continued until homogenous. The mixture was then wet milled using a bead mill to particle size around 2 μm.

| | Amount (wt/wt %) |
|---|---|
| Afidopyropen | 1.5 |
| Dinotefuran | 15 |
| Cosurfactant A | 15 |
| Block Polymer A | 14.6 |
| Alkoxylate B | 32 |
| Chemical stabilizer | 0.2 |
| Thickener | 1.7 |
| 1,2-propylene glycol | 20 |

Samples were stored and analyzed as in Example 1. It was found there was no increase in particle size at all storage temperatures and no phase separation occurred, therefore, the suspension was physically stable.

Example 6: Broflanilide Suspension in Propylene Glycol

Afidopyropen and formulation additives (except Thickener) were added winto 1,2-propylene glycol while agitating. The agitation was continued until afidopyropen was completely dissolved. Then broflanilide and Thickener was added into the mixture while agitating. The agitation was continued until homogenous. The mixture was then wet milled using a bead mill to particle size around 2 μm.

| | Amount (wt/wt %) |
|---|---|
| Afidopyropen | 1.5 |
| Broflanilide | 15 |
| Cosurfactant A | 14 |
| Block Polymer A | 16.3 |
| Alkoxylate B | 30 |
| Chemical stabilizer | 0.2 |
| Silica Thickener | 1 |
| 1,2-propylene glycol | 22 |

Samples were stored and analyzed as in Example 1. It was found there was no increase in particle size at all storage temperatures and no phase separation occurred, therefore, the suspension pension was physically stable.

Example 7: Broflanilide and Insecticide A Suspension in Propylene Glycol

Broflanilide, Insecticide A, and all formulation additives were added into 1,2-propylene glycol while agitating. The agitation was continued until homogenous. The mixture was then wet milled using a bead mill to particle size around 2 μm.

| | Amount (wt/wt %) |
|---|---|
| Broflanilide | 10 |
| Insecticide A | 10 |
| Cosurfactant A | 14 |
| Block Polymer A | 12 |
| Alkoxylate B | 20 |
| Thickener | 1 |
| 1,2-propylene glycol | 33 |

Samples were stored and analyzed as in Example 1. It was found there was no increase in particle size at all storage temperatures and no phase separation occurred, therefore, the suspension was physically stable.

Example 8: Broflanilide and Insecticide B Suspension in Propylene Glycol

The Example 7 was repeated with Insecticide B instead of Insecticide A. Again, it was found there was no increase in particle size at all storage temperatures and no phase separation occurred, therefore, the suspension was physically stable.

Example 9: Broflanilide and Insecticide C Suspension in Propylene Glycol

The Example 7 was repeated with Insecticide C instead of Insecticide A. Again, it was found there was no increase in particle size at all storage temperatures and no phase separation occurred, therefore, the suspension was physically stable.

The invention claimed is:

1. A liquid nonaqueous composition comprising: a pesticide in form of suspended particles, at least 10 wt % of a water soluble solvent, up to 10% of a water-insoluble organic solvent, an inorganic thickener, and an alkoxylate, wherein the composition comprises less than 5 wt. % water and further wherein a sum of the amounts of the water soluble solvent and the alkoxylate is at least 40 wt % based on the total weight of the composition.

2. The composition according to claim 1, wherein the water soluble solvent comprises one or more of the following: propylene glycol, ethylene glycol, polyethylene glycol, polypropylene glycol, glycerin, propylene carbonate, ethylene carbonate, butylene carbonate, and dimethyl sulfoxide.

3. The composition according to claim 1 comprising at least 10 wt % of the alkoxylate based on the total weight of the composition.

4. The composition according to claim 1, wherein the alkoxylate is an alkoxylated alkanol.

5. The composition according to claim 1, comprising from 0.01 to 5.0 wt % of the inorganic thickener based on the total weight of the composition.

6. The composition according to claim 1, wherein the inorganic thickener comprises silica particles.

7. The composition according to claim 1, further comprising a block polymer surfactant.

8. The composition according to claim 7, comprising at least 5 wt % of the block polymer surfactant.

9. The composition according to claim 7, where the block polymer surfactant is an alkoxylate block polymer of an A-B-A type comprising blocks of polyethylene oxide (block "A") and polypropylene oxide (block "B"), and wherein the alkoxylate block polymer is terminated on both ends by hydroxyl groups.

10. The composition according to claim 7, wherein the sum of the amounts of the water soluble solvent, the alkoxylate, and the block polymer surfactant is at least 50 wt % based on the total weight of the composition.

11. The composition according to claim 1, further comprising a nonionic cosurfactant selected from phenol alkoxylates.

12. The composition according claim 11, comprising 5 to 25 wt % of the nonionic cosurfactant.

13. The composition according to claim 1, comprising less than 1 wt % of water.

14. A method for the preparation of the composition as defined in claim 1, the method comprising contacting the pesticide with the water soluble solvent, up to 10% of the water-insoluble organic solvent, the inorganic thickener, and the alkoxylate.

15. A method for controlling phytopathogenic fungi and/or undesired plant growth and/or undesired attack by insects or mites and/or for regulating the growth of plants, wherein the composition as defined in claim 1 is allowed to act on a pest, their habitat or plants to be protected from the pest, on soil and/or on undesired plants and/or useful plants and/or their habitat.

16. The method according to claim 14, further comprising contacting a block polymer surfactant with the pesticide, the water soluble solvent, the inorganic thickener, and the alkoxylate.

17. The method according to claim 14, further comprising contacting a nonionic cosurfactant with the pesticide, the water soluble solvent, the inorganic thickener, and the alkoxylate.

18. The method according to claim 14, further comprising contacting a block polymer surfactant and a nonionic cosurfactant with the pesticide, the water soluble solvent, the inorganic thickener, and the alkoxylate.

19. The composition according to claim 1, wherein the composition is essentially free of water-insoluble organic solvent.

* * * * *